United States Patent
Harmenberg et al.

(12)

(10) Patent No.: US 6,337,324 B1
(45) Date of Patent: *Jan. 8, 2002

(54) PHARMACEUTICAL COMBINATION

(75) Inventors: Johan Georg Harmenberg, Stockholm; Ann Harriet Margareta Kristofferson, Södertälje, both of (SE)

(73) Assignee: Medivir, AB, Huddinge (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/612,847
(22) PCT Filed: Feb. 2, 1996
(86) PCT No.: PCT/SE96/00124
§ 371 Date: Mar. 8, 1996
§ 102(e) Date: Mar. 8, 1996
(87) PCT Pub. No.: WO96/24355
PCT Pub. Date: Aug. 15, 1996

(30) Foreign Application Priority Data

Feb. 6, 1995 (WO) ............................... PCT/SE95/00114

(51) Int. Cl.[7] .............................................. A61K 31/56
(52) U.S. Cl. ........................... 514/171; 514/75; 514/81; 514/82; 514/85; 514/120; 514/179
(58) Field of Search ................. 514/179, 171, 514/75; 518/85, 81, 82, 120

(56) References Cited

U.S. PATENT DOCUMENTS

| | | | |
|---|---|---|---|
| 3,317,384 A | 5/1967 | Underwood | 167/58 |
| 4,512,978 A | 4/1985 | Inwood | 424/145 |
| 4,610,868 A | 9/1986 | Fountain et al. | 424/1.1 |
| 6,068,860 A * | 5/2000 | Carlsson et al. | 424/601 |

FOREIGN PATENT DOCUMENTS

| | | | | |
|---|---|---|---|---|
| AU | 0636255 | * | 5/1992 | A61K/31/66 |
| AU | 636255 | | 4/1993 | A61K/31/66 |
| EP | 0350287 | | 1/1990 | A61K/31/70 |
| EP | 0594223 | | 4/1994 | A61K/31/70 |
| WO | 9219244 | | 11/1992 | A61K/31/57 |
| WO | 9503805 | | 2/1995 | A61K/31/52 |
| WO | 9527501 | | 10/1995 | A61K/38/21 |

OTHER PUBLICATIONS

Alenius, S., et al; Therapeutic Effects of Foscarnet Sodium and Acyclovir on Cutaneous Infections due to Herpes Simplex Virus Type 1 in Guinea Pigs, J. Inf. Dis. 1982; 145:569–73.

The Human Herpesviruses, ed. Roizman et al. 1993, Whitely, Richard et al.; The epidemiology and Clinical Manifestations of Herpes Smplex Virus Infections.

Kristofferson, A. et al.; Limited Efficacy of Inhibitors of Herpes Simplex Virus DNA Synthesis in Murine Models of Recrudescent Disease, J. Gen. Virol. (1988), 69, 1157–1166.

Schinazi, R.F. et al; Studies In Vitro and In Vivo of Combinations of Antivirals and Antiinflammatory Agents in Relation to the Treatment of Herpes Simplex Viruses, Current Chemotherapy and Immunotherapy, 12th Int. Congress, Florence, Jul. 1981.

From Chemical Abstracts, vol. 112, nr. CA:125021: Loftsson, T.; Effect of choline esters and oleic acid on the penetration of acyclovir, estradiol, hydrocortisone, nitroglycerin, retinoic acid and trifluorothymidine across hairless mouse skin in vitro, Acta Pharm. Nor. (1989), 1(5), 279–86.

From Chemical Abstracts, vol. 112, nr 4, (dissertation): Choi, Hoo Kyun: Enhanced transdermal delivery of propanolol, hydrocortisone, acyclovir and peptide–type drugs (1989).

Power, W J et al., Acyclovir ointment plus topical betamethasone or placebo in first episode disciform keratitis, British Journal of Ophtalmology 1992; 76:711–713.

McGill, J. Herpes zoster ocular infection, Scand. J. Infect. Dis. Suppl. 46: 85–88, 1985.

ABPI Compendium of Data Sheets and Summaries of Product Characteristics, 1996–97, Datapharm Publications Ltd., pp. 390 and 1271.

Berkow, et al., The Merck Manual of Diagnosis and Therapy, 14th Edition, pp. 2023–2025 (1982).

Chemical Abstract No. 97: 156002r from Schinazi, et al., Curr. Chemother. Immunother. 2, 1085–1087 (1982).*

Merck Index 10th Ed #140, #4135, #1435, 1984.*

Notter et al, 89 CA:157769t, 1978.*#jf139##

Primary Examiner—Frederick Krass
(74) Attorney, Agent, or Firm—White & Case LLP

(57) ABSTRACT

The invention relates to pharmaceutical compositions for topical administration comprising a topically acceptable antiviral substance and an antiinflammatory glucocorticoid in a pharmaceutically acceptable carrier. The pharmaceutical composition can be used in the prophylactic and curative treatment of herpesvirus infections in mammals including man. The invention also relates to the use of a combination of a topically acceptable antiviral substance and an antiinflammatory glucocorticoid for the manufacture of a medicament for said prophylactic and curative treatment.

36 Claims, 3 Drawing Sheets

PHARMACEUTICAL COMBINATION

This application is a 371 of PCT/SE96/00124, filed Feb. 2, 1996.

FIELD OF THE INVENTION

The present invention relates to a pharmaceutical composition for topical administration suitable for the prophylaxis and treatment of herpesvirus infections. The pharmaceutical composition comprises a combination of an antiviral agent and an antiinflammatory agent and can preferably be used for the treatment of recurrent herpesvirus infections.

BACKGROUND OF THE INVENTION

Herpesvirus infections in humans can be caused by different human herpesviruses, the most common being herpes simplex virus and varicella-zoster virus. There are also many animal herpesviruses.

Following a primary infection with herpes simplex virus or varicella-zoster virus, the virus establishes latency in the sensory nerve cells for the rest of the patient's life and can subsequently be reactivated repeatedly. Following a reactivation in the nerve cell, the virus is transported through the nerves to the skin and subsequently a lesion develops. One characteristic of herpesvirus infection is the inflammation which follows immediately upon an outbreak of virus replication. The inflammation contributes to all symptoms associated with herpesvirus recurrence including redness, swelling, itching and pain as well as lesions.

Herpes simplex viruses can be divided into two serotypes, HSV type 1 (HSV-1) and type 2 (HSV-2), the clinical manifestations of which range from benign self-limiting orofacial and genital infections to potentially life threatening conditions such as encephalitis and generalized neonatal infections.

Oral-facial HSV infections are primarily caused by HSV-1. Following a primary infection in childhood the virus becomes latent. After reactivation a recurrent oral-facial HSV infection develops, which is more commonly known as a cold sore. About half of the patients experience prodromal symptoms such as pain, burning or itching at the site of the subsequent lesions. The condition is generally rapidly self-limiting and a typical episode will heal in around 10 days from the first symptoms. Viral replication in the lip is initiated early and maximum virus load is attained 24 hours after the onset of the reactivation. The virus concentration is then dramatically reduced and typically virus cannot be isolated 70–80 hours after the onset.

The clinical presentation of genital HSV infections is similar to the oral-facial infections with some important exceptions. Genital HSV infections are most often caused by HSV-2 and following the primary infection the virus will latently infect sensory or autonomic ganglions. Reactivation will produce the local recurrent lesions on or near the genitals that are characteristic of the herpes infection.

A primary infection with varicella-zoster virus (VZV) causes chicken-pox. Like HSV, VZV becomes latent following the primary infection and can be activated as herpes zoster later on in life. Zoster usually results in skin rash and intensive acute pain. In 30% of the patients, the pain can be prolonged and continue for weeks or months after the rash has cleared up.

HSV and VZV may, in addition to mucous or cutaneous manifestations, also cause keratitis in the eyes. This condition is also recurrent and may cause blindness.

There are a number of antiviral agents which are active against the human herpesviruses. There has, however, so far been limited clinical success in the treatment of recurrent herpesvirus infections.

Foscarnet, that is the hexahydrate of the trisodium salt of phosphonoformic acid or sodium phosphonoformate hexahydrate, and acyclovir are well-known antiviral compounds, which as topical formulations have been extensively tested against recurrent herpes simplex virus infections in clinical trials with only a moderate degree of success. Acyclovir has, in addition, been tested as an oral formulation against recurrent HSV infections with significant but limited clinical effect if used after the appearance of symptoms. As a result of such a treatment the healing time will be shortened by no more than approximately one day. The inhibitory effect of foscarnet, as well as that of acyclovir, against herpes viruses in vitro is, however, high.

Standard-dose acyclovir shows little effect against VZV infections in the clinic. High-dose acyclovir shows significant but limited effect on zoster lesions if treatment is initiated within 72 hours from the appearance of the first symptoms.

Other antiviral substances, which have been used topically and which exhibit an inhibitory effect against HSV in vitro, are for example adenine arabinoside (ara-A, vidarabine), arabinosyladenine-monophosphate (ara-AMP), lobucavir (bishydroxymethylcyclobutylguanine, BHCG), brivudine (bromovinyldeoxyuridine, BVDU), desciclovir, famciclovir, cidofovir (HPMPC, GS504), idoxuridine, netivudine (zonavir, BW882C87), penciclovir, PAA (phosphonoacetate), PFA (phosphonoformate), sorivudine (brovavir, BV-araU), trifluridin (trifluorothymidine, TFT), tromantadine, valacyclovir, virend, 1-docosanol (lidakol), 348U87, 2242 (2-amino-7-(1,3-dihydroxy-2-propoxymethyl)purine), HOE 961, civamide (capsaicin), PMEA (9-(2-phosphonylmethoxyethyl)adenine), peptide T, BILD 1263, CRT.

Clinical primary infections with human herpes simplex viruses differ in a number of important aspects from subsequently reactivated infections. The viral shedding period is longer in the primary infection (about 10 days in labial and 3 weeks in genital infection) compared with reactivated infection (3–4 days for both labial and genital infections). Following termination of the viral shedding period in primary infections the lesion will heal in a few days while in the case of reactivated infections, the inflammation continues after viral replication has ceased and the clinical symptoms will remain for another week.

Obviously a reduction of virus multiplication in itself will not substantially alter the clinical course of a recurrent herpes infection. It is, therefore, not surprising that antiviral drugs when tested in clinical trials show a more substantial effect against a primary infection as compared with reactivated infections, such as recurrent herpes labialis or genitalis. Because of the rapid self-limiting nature of the virus shedding period in recurrent HSV infection the improvement of only one day healing time obtained in clinical trials with antiviral drugs is not surprising.

Different antiinflammatory agents have been tested to treat the inflammation that accompanies the recurrent infection, but only with limited success. Traditionally, inflammatory conditions in the eye, such as keratitis, have been treated with steroids. Even though this type of compounds is known to potentially promote herpesvirus replication steroids have been used in severe cases, for instance to save the patients vision. This practice has been controversial.

In summary, there has been little clinical success in the treatment of recurrent herpesvirus infections even with the most potent antiviral drugs. There is, thus, a great need for effective drugs and methods of treatment for recurrent herpes infections.

PRIOR ART

AU 636 255 refers to topical treatment of for instance herpes simplex infections by means of a composition comprising an antiviral pentosan polysulphate and an antiinflammatory or antioxidant drug. The antiinflanmmatory drugs are different salicylates or bufexamal, that is NSAIDs.

U.S. Pat. No. 3,317,384 discloses a combination of a glucocorticoid and an antiviral nucleoside, ara-C or ara-A or analogues thereof, for topical pharmaceutical applications, mainly for ocular administration. The systemic toxicity of the antiviral compounds is too high to allow for an application to the skin or mucous membrane.

Power, W. J., et al., British Journal of Ophthalmology 1992; 76:711–713, reports a treatment of patients with disciform keratitis with either 3% acyclovir ointment and 0.1% betamethasone drops or acyclovir ointment and matching placebo. It was concluded that the healing time as well as other clinical parameters improved more favourably in the combination treatment group.

On the other hand McGill, J.: Herpes zoster ocular infection, Scand J Infect Dis Suppl 1985; 47: 85–8 reports an analysis of patients with herpes zoster ocular infection carried out to determine the effect of treatment with either topical acyclovir, topical steroid or a combination of both. It was found that acyclovir was superior to steroids and to the combination.

DISCLOSURE OF THE INVENTION

It has now surprisingly been found that recurrent herpesvirus infections can be treated by topical administration of a combination of a topically acceptable antiviral substance and an antiinflammatory glucocorticoid.

The invention relates to a pharmaceutical composition for topical administration comprising a combination of a topically acceptable antiviral substance and an antiinflammatory glucocorticoid in a pharmaceutically acceptable carrier.

Antiviral substances suitable for the purposes of the present invention are topically acceptable antiviral compounds which in addition to being specific inhibitors of herpesvirus multiplication, also are active after topical administration and in addition pharmaceutically acceptable for topical administration. This means that the toxicity of the antivirals must be sufficiently low to allow for a continuous contact with the human body and in particular with the skin and mucous membranes.

Antiviral substances can be selected from the group comprising compounds acting on viral DNA polymerase, such as nucleoside analogues after phosphorylation to their triphosphate forms; phosphonoformic and phosphonoacetic acids and their analogues; and other antiviral compounds having a different mechanism of action. As examples of antiviral substances which can be used in the combination of the invention can be mentioned acyclovir (ACV), ACV-phosphonate, brivudine (bromovinyldeoxyuridine, BVDU), carbocyclic BVDU, buciclovir, CDG (carbocyclic 2'-deoxyguanosine), cidofovir (HPMPC, GS504), cyclic HPMPC, desciclovir, edoxudine, famciclovir, ganciclovir (GCV), GCV-phosphonate, genivir (DIP-253), H2G (9-[4-hydroxy-2-(hydroxymethyl)butyl]guanine), HPMPA, lobucavir (bishydroxymethylcyclobutylguanine, BHCG), netivudine (zonavir, BW882C87), penciclovir, PMEA (9-(2-phosphonylmethoxy-ethyl)adenine), PMEDAP, sorivudine (brovavir, BV-araU), valacyclovir, 2242 (2-amino-7-(1,3-dihydroxy-2-propoxymethyl)purine), HOE 602, HOE 961; BPFA (batyl-PFA), PAA (phosphonoacetate), PFA (phosphonoformate); arildone, amantadine, BILD 1263, civamide (capsaicin), CRT, ISIS 2922, peptide T, tromantadine, virend, 1-docosanol (lidakol) and 348U87 (2-acetylpyridine-5-[2-chloro-anilino-thiocarbonyl]-thiocarbonohydrazone).

Preferred antiviral substances are those with specific antiviral activity such as herpes specific nucleoside analogues which are preferentially phosphorylated in virus-infected cells and have very low or non-existent incorporation into cellular DNA as well as other compounds with specific antiviral activity. Acyclovir, for instance, has a selectivity ratio for the inhibitory activity against HSV-1 in vitro of about 2000. Among said preferred substances can in addition to acyclovir be mentioned brivudine, cidofovir, desciclovir, famciclovir, ganciclovir, HOE 961, lobucavir, netivudine, penciclovir, PMEA, sorivudine, valacyclovir, 2242, BPFA, PFA, PAA.

Especially preferred are foscarnet and acyclovir.

PFA, as used in this specification and claims, refers in addition to foscarnet, that is the hexahydrate of the trisodium salt of phosphonoformaic acid, also to other pharmaceutically acceptable salts, esters or other derivatives of phosphonoformic acid in hydrated or non hydrated form. In the same way the stated antiviral substances also refer to salts, esters and other derivatives thereof, whenever applicable.

Some topically active antiviral substances, such as the nucleoside analogues idoxuridine and trifluorothymidine, adenine arabinoside (ara-A, vidarabine) and arabinosyladenine-monophosphate (ara-AMP), which can be used for the treatment of herpetic conditions in the eye are not contemplated within the scope of this invention as having too high a toxicity for application to the skin and mucous membrane. This toxicity is due to the lack of antiviral specificity, that is said compounds are phosphorylated in uninfected as well as infected cells and incorporated into cellular DNA.

It could be of advantage to utilize two or more antivirals or to combine the antiviral with an adjuvant or other additive in order to increase the effect on the herpesvirus to be treated, for instance in cases of resistance developed to a particular antiviral substance.

The antiinflammatory glucocorticoid suitable for the purposes of the present invention can be a naturally occurring or a synthetic topical glucocorticoid that is glucocorticosteroid. The glucocorticoids can be selected from any of the Group I–III glucocorticoids, according to a classification system for topical glucocorticoids used in the Nordic countries, corresponding to less potent, low or moderately potent glucocorticoids. Examples of glucocorticosteroids are alclometasone, amicinonide, beclomethasone, betamethasone, budesonide, ciclesonide, clobetasone, clocortolone, cloprednol, cortison, desonide, desoximethasone, dexamethasone, diflorosane, diflucortolone, difluprednate, fludrocortisone, fludroxycortid, flumethasone, flunisolide, fluocinolone acetonide, fluocinonide, fluocortin, fluocortolone, fluprednidene, fluticasone, halcinonide, halobetasol, halometasone, hydrocortisone, methylprednisolone, mometasone, paramethasone, prednisolone, prednicarbate, prednisone, prednylidene, rofleponide, tipredane and triamcinolone and their esters, salts and solvates, that is hydrates, where applicable.

Preferred glucocorticoids are hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide.

A preferred embodiment of the invention is a pharmaceutical composition comprising foscarnet and hydrocortisone; in another embodiment the pharmaceutical compositon comprises foscarnet and budesonide.

Still another preferred embodiment of the invention is a pharmaceutical composition comprising acyclovir and hydrocortisone; in another embodiment the pharmaceutical composition comprises acyclovir and fluticasone.

The carrier system should be stable and pharmaceutically and cosmetically acceptable. It should also enable incorporation of sufficient amounts of the active ingredients to give the proper penetration characteristics. In addition to conventional ingredients in creams, lotions, gels or ointments, compositions based on phospholipids, including sphingolipids can be advantageous.

A pharmaceutical composition of the invention can be used for the prophylaxis and/or treatment of herpesvirus infections in mammals including man. In a preferred embodiment the composition is used for the treatment of recurrent herpesvirus infections. The curative treatment of recurrent infection should take place during the virus replication, preferably from the first appearance of prodromal symptoms and for a period of 3–4 days at least. It might be of advantage to apply the formulation during the whole episode, every second hour or ad lib. Lesions should be treated the same way. The frequency of application will be of the order of 1–10 applications per day, preferably every 8 hour, until healing is completed. Prophylactic treatment could be an alternative in patients with regularly recurrent disease. In this case the formulation should be applied to the area where a recurrence is expected before the appearance of the first symptoms.

The compositions of the invention can be used to treat all types of herpesvirus, as well as other viruses, which are inhibited by the antiviral substance and which replicate in the skin or the mucous membrane. As exemples of said viruses can be mentioned HSV-1, HSV-2 and VZV.

The pharmaceutical compositions for topical administration according to the present invention are preferably creams, lotions, gels, ointments or drops. The pharmaceutical compositions can be incorporated into plasters or patches to be applied to the skin of a patient to be treated for herpes infections or into pens or sticks for application to the skin or mucous membranes.

Topical administration refers in this context to dermal or mucosal administration to the skin or mucous membrane.

Due to the herpesvirus-stimulating effects of glucocorticoids, care must be taken to define the optimal dose of the respective components. Too high a dose of the glucocorticoid might stimulate virus multiplication to an extent that can not be inhibited by the antiviral substance. With too low a dose the desired reduction of the symptoms of inflammation might not be achieved.

The mutual relationship between the two active substances will be different for different combinations of substances. The relative amount of the antiviral substance in a pharmaceutical composition according to the present invention can be within the range of 0.1–10% (w/w), preferably 1–5% (w/w). The antiinflammatory glucocorticoid concentration can be within the range of 0.005–3% (w/w) depending on the potency of the respective compound. A pharmaceutical composition containing a combination of foscarnet and hydrocortisone could preferably comprise 0.3–3% foscarnet and 0.25–1% hydrocortisone. A corresponding composition containing acyclovir and hydrocortisone preferably comprises 1–5% acyclovir and 0.25–1% hydrocortisone.

In another aspect the invention also refers to the use of a combination of a topically acceptable antiviral substance and an antiinflammatory glucocorticoid for the manufacture of a medicament for topical treatment of recurrent herpesvirus infections in mammals including man.

In another aspect, the present invention refers to a method of prophylactic and/or curative treatment of herpesvirus infections of the skin or mucous membranes in mammals including man comprising topical administration, in combination or in sequence, of a therapeutically effective dose of a topically acceptable antiviral substance and of an antiinflammatory glucocorticoid.

In yet another aspect the pharmaceutical compositions of the present invention can also be used as a cosmetic composition to improve the appearance of a human suffering from an oral-facial HSV infection by application of an effective amount of said compositions to the lesions or rash.

The topical administration of the pharmaceutical compositions of the present invention have resulted in a significantly better pharmacological effect in the treatment of recurrent herpes infections than the administration of conventional topical compositions comprising an antiviral compound as the only active substance. This has been determined in biological tests by means of a new animal model described below.

PHARMACEUTICAL COMPOSITIONS

EXAMPLE 1

Cream of Foscarnet 3%

Figure 1:
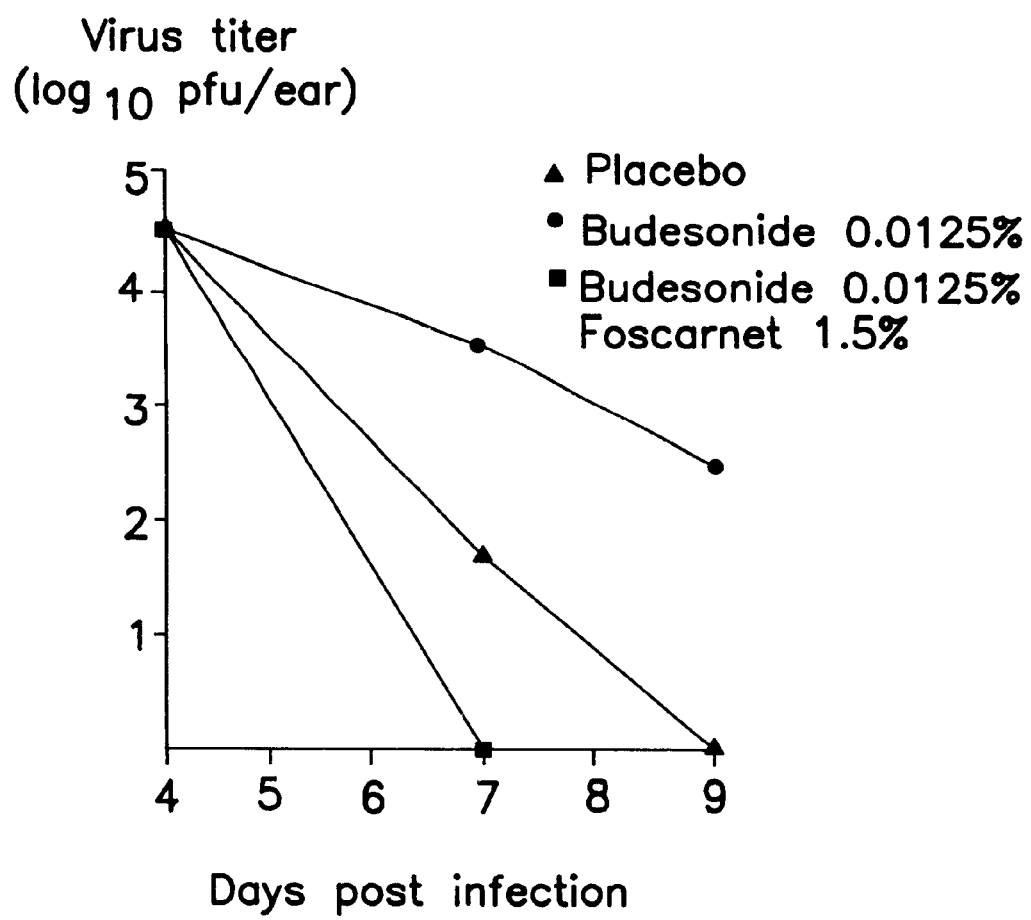
FIG. 1 Effects of topical treatment with budesonide and foscarnet+budesonide on days 4–7 after infection in comparison with placebo on mean HSV-titers in the pinna of neck-infected Balb/C mice (n=10) after adoptive transfer of immunity on day 2 after infection.

Foscarnet cream was prepared as described by Alenius, S. et al., "Therapeutic effects of foscarnet sodium and acyclovir on cutaneous infections due to herpes simplex virus type 1 in guinea pigs", J. Inf. Dis. 1982; 145:569–73). In the following said cream, with a content of 3% foscarnet and the composition as stated below, is referred to as Foscarnet Cream:

|  | Amount (mg) |
| --- | --- |
| Trisodium phosphonoformate hexahydrate | 30 |
| Polyoxyethylene fatty acid ester | 44 |
| Cetyl alcohol | 20 |
| Stearic acid | 20 |
| Paraffin liquid | 20 |
| Propylene glycol | 20 |
| Glycerol | 15 |
| Methyl p-hydroxybenzoate | 0.7 |
| Propyl p-hydroxybenzoate | 0.3 |
| Water | ad 1000 |

The cream base without foscarnet is used as the placebo cream. To the placebo cream can be added foscarnet in an amount of 3–30 mg as well as micronized hydrocortisone in an amount of 2.5–10 mg for the preparation of a cream of 0.3–3% foscarnet and 0.25–1% hydrocortisone.

EXAMPLE 2
Cream of Budesonide 0.0125% and Foscarnet 1.5%

By simple mixing of Foscarnet Cream and budesonide cream (0.025%, Preferid®, Gist-Brocades, The Netherlands) a combination cream was obtained having the following composition:

|  | Amount (mg) |
| --- | --- |
| Budesonide | 0.125 |
| Trisodium phosphonoformate hexahydrate | 15 |
| Sodium citrate | 0.6 |
| Citric acid | 0.3 |
| Sorbic acid | 0.3 |
| Cetostearyl alcohol | 30 |
| Paraffin liquid | 3 |
| Cetomacrogol 1000 | 6 |
| White soft paraffin | 15 |
| Arlatone (polyoxyethylene fatty acid ester) | 31 |
| Cetyl alcohol | 14 |
| Stearic acid | 14 |
| Mineral oil | 14 |
| Propylene glycol | 14 |
| Glycerol | 10.5 |
| Methyl p-hydroxybenzoate | 0.43 |
| Propyl p-hydroxybenzoate | 0.19 |
| Sodium hydroxide 2 M* |  |
| Hydrochloric acid 2 M* |  |
| Water | ad 1000 |

*For adjusting pH to 7–8

COMPARATIVE EXAMPLE 3
Cream of Foscarnet 1.5% and Lidocaine 1%

By simple mixing of Foscarnet Cream (3%) and lidocain cream (2%, Xylocain®, Astra AB, Sweden) a combination cream was obtained having the following composition:

|  | Amount(mg) |
| --- | --- |
| Lidocaine | 10 |
| Trisodium phosphonoformate hexahydrate | 15 |
| Miglyol 812 | 27.6 |
| Arlatone (polyoxyethylene fatty acid ester) | 44.2 |
| Carboxypolymethylene | 2 |
| Cetyl alcohol | 16 |
| Stearic acid | 16 |
| Mineral oil | 16 |
| Propylene glycol | 16 |

|  | Amount(mg) |
| --- | --- |
| Glycerol | 12 |
| Methyl p-hydroxybenzoate | 0.49 |
| Propyl p-hydroxybenzoate | 0.22 |
| Sodium hydroxide 2 M* |  |
| Hydrochloric acid 2 M* |  |
| Water purified | ad 1000 |

*For adjusting pH to 7–8

EXAMPLE 4
Cream of Hydrocortisone 1%

|  | Amount (mg) |
| --- | --- |
| Hydrocortisone | 10 |
| Methyl p-hydroxybenzoate | 2.0 |
| Propyl p-hydroxybenzoate | 0.5 |
| Glycerol | 0.03 |
| Ethanol | 5 |
| Isopropylmyristate | 50 |
| Amphisol | 10 |
| Paraffin | 30 |
| Paraffin, liquid | 40 |
| Macrogol stearate | 100 |
| Cetyl alcohol | 50 |
| Water | ad 1000 |

This cream is commercially available as Hydrokortison kräm 1% ACO, Kabi Pharmacia AB, Sweden.

EXAMPLE 5
Cream of Foscarnet 2.4% and Hydrocortisone 1%

|  | Amount (% by weight) |
| --- | --- |
| Trisodium phosphonoformate hexahydrate | 2.4 |
| Hydrocortisone | 1 |
| Phospholipids | 30 |
| Water | ad 100 |

EXAMPLE 6
Cream of Acyclovir 5%

|  | Amount (mg) |
| --- | --- |
| Acyclovir | 50 |
| Propylene glycol | 400 |
| Poloxamer | 10 |
| Cetylstearyl alcohol | 67.5 |
| Paraffin |  |
| Paraffin, liquid |  |
| Sodium dodecyl sulphate |  |
| Water | ad 1000 |

This cream is commercially available as Zovirax® Creme 5% from Wellcome GmbH, Germany.

Biological Tests

A primary herpes infection is characterized by a rapid and comparatively long-lasting phase of viral replication and a slower and less pronounced immune response causing only a low degree of inflammation. In a typical primary HSV infection shedding of virus continues for around 20 days, while in a recurrent infection virus shedding ceases after only 3 or 4 days (Whitley, R. J. and Gnann, J. W. in The Human Herpesviruses, Ed. Roizman et al., 1993). The common recurrent HSV and VZV infections are characterized by a strong and rapid immune response and inflammation causing clinical symptoms such as pain, redness and swelling. The immune response also rapidly limits the local virus replication, and typically 3–4 days after the first symptoms virus can no longer be isolated from lesions. In order to represent the clinical situation of recurrent HSV or VZV infections a new type of animal model has been used, as described below. Said model includes the induction of immune response in the animal before the administration of the composition to be tested.

Animal Model for Recurrent Herpes Infection

In the novel animal model, virus is inoculated in the neck of a mouse. The virus will then be transported through the nerves to the skin of the corresponding ear. This transport will take approximately 3–4 days. On day 2 the animals are given immune cells with reactivity against the infecting virus. Subsequently, when the virus arrives at the ear, the animal instantly mobilises an effective immune response against the virus, thus mimicking the clinical situation of a recurrent herpes infection.

Human HSV-1 ($2 \times 10^5$ plaque forming units, pfu, strain C42 or SC16) is inoculated into the neck of groups of 10–18 female in-bred Balb/C mice (16–18 g) as described by Kristofferson et al. ("Limited efficacy of inhibitors of herpes simplex virus DNA synthesis in murine models of recrudescent disease", J. Gen. Virol. 1988; 69:1157–66). The development of zosteriform spread infection is then recorded by daily inspection of the occurrence of lesions on the pinna and swelling of the ear.

The lesions are scored on a scale from 0 to 4 as follows:
0: no lesions on the ear
1: isolated zosteriform lesions on the ear
2: mild ulceration of zosteriform lesions on the ear
3: moderate ulceration of zosteriform lesions on the ear
4: severe ulceration of zosteriform lesions on the ear Swelling of the ear was assessed by measuring the thickness of the ears using an engineers micrometer, as described by Kristofferson et al. The titre of infectious virus in the ear was measured as described by Kristofferson et al, except that BHK (baby hamster kidney) cells were used in addition.

On day 2 after infection the animals are given adoptive transfer of immunity, ATI, against HSV-1 by intravenous injection of $2 \times 10^7$ lymph node cells into the tail. Said lymph node cells had been prepared by injecting HSV-1 ($10^5$ pfu, strain C42 or strain SC16) into the pinna of both ears of anaesthetized female Balb/C mice (16–18 g). Seven days post infection the animals are sacrificed by cervical dislocation, the draining lymph nodes are removed, and a suspension of lymph node cells in phosphate buffered saline is prepared by means of a micromesh.

ATI decreases the virus titers in the ear of the infected animals, as well as the duration of virus shedding. However, ear swelling and lesion score of the ears is increased by ATI. Swelling is believed to correspond to inflammation and it is apparent that ATI worsens inflammation and lesion score even though virus is much more rapidly cleared.

On day 4 after the infection and for 4 days, a composition to be tested as to activity against recurrent herpes is distributed equally in an amount of approximately 25 mg of cream on each side of the ear, every 8 h.

Experiment 1. Test of Combination Creams of Foscarnet and an Antiinflammatory Substance Budesonide and lidocaine were selected for testing as examples of antiinflammatory compounds.

The foscarnet cream Foscarnet Cream was prepared as described in Example 1. The cream base without drug was used as placebo.

The cream base described above was also mixed with budesonide cream (0.025%, Preferid®, Gist-Brocades, The Netherlands) to obtain suitable concentrations for treatment. For the experiments using a combination cream of foscarnet (1.5%) and budesonide (0.0125%), the formulation resulting from a mixing of the creams is described in Example 2.

A lidocaine cream (2%, Xylocain®, Astra AB, Sweden) was also mixed with the foscarnet cream and the resulting formulation of foscarnet (1.5%) and lidocaine (1%) is described in Comparative Example 3.

Foscarnet, the two antiinflammatory substances, as well as the two combination creams were tested in the animal model described, with ten animals in each group. The respective cream was applied day 4–7 after infection three times daily. The lesion score and ear thickness were recorded daily on days 4–12, 15 and 21 after infection and the mean cumulative values±standard deviation calculated for said period. The results are given in Table 1 with the percent compared to placebo in parenthesis (values for placebo treated animals were set to 100%). Values significantly different from placebo-treated animals are indicated with an asterisk ($p=0.0001$).

TABLE 1

| Formulation | Compounded value ± s.d. (% of placebo) Lesion score | Compounded value ± s.d. (% of placebo) Ear thickness (mm) |
| --- | --- | --- |
| Placebo | 9.2 ± 1.6 (100) | 3.6 ± 0.3 (100) |
| Foscarnet | 7.5 ± 2.5 (82) | 3.0 ± 0.4 (83) |
| Budesonide | 8.8 ± 1.8 (96) | 2.1 ± 0.4 (58)* |
| Lidocaine | 9 ± 2 (98) | 3.6 ± 0.3 (100) |
| Foscarnet + Budesonide | 5.3 ± 0.8 (58)* | 1.6 ± 0.1 (45)* |
| Foscarnet + Lidocaine | 9 ± 1.5 (98) | 3.5 ± 0.3 (97) |

Budesonide cream alone decreased the cumulative ear thickness to 58% of placebo-treated animals, while lidocaine cream had no effect. The combination of foscarnet and budesonide reduced ear thickness to 45%, compared to placebo. The combination of foscarnet and lidocaine had no effect on ear thickness or lesion score.

Treatment with a topical formulation of budesonide increased the virus titers in the ears on day 7 and day 9 after infection between 100- and 1000-fold as compared with placebo treatment (FIG. 1). More specifically, the virus titers in the ears were dramatically reduced when the combination was used compared with placebo or budesonide cream (FIG. 1). No virus could be detected in the animals treated with the combination of foscarnet and budensonide on day 7 after infection.

Figure 2:
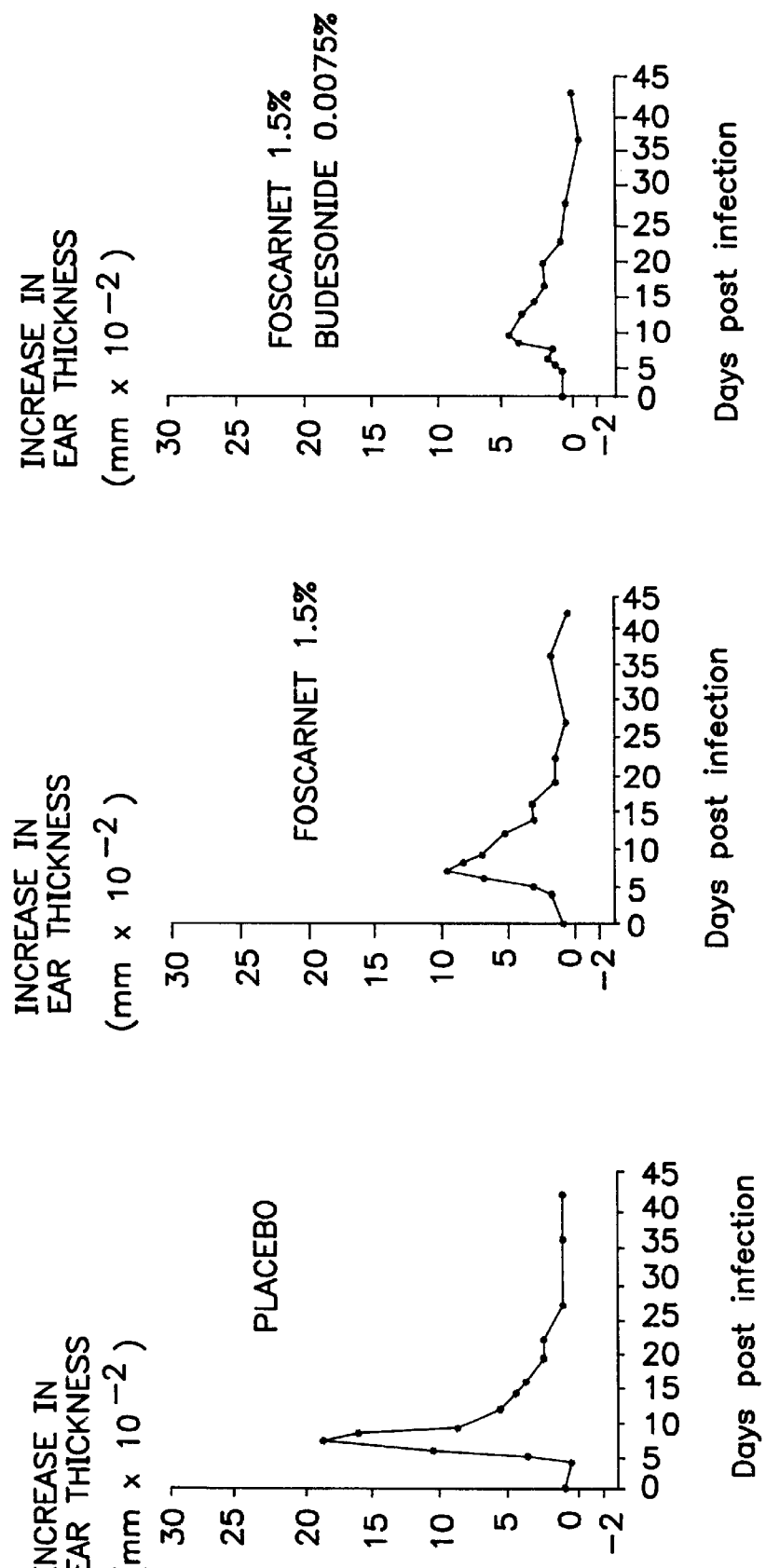
FIG. 2 Effects of topical treatment with foscarnet and foscarnet+budesonide on days 4–7 after infection in comparison with placebo on median ear swelling of neck-infected Balb/C mice (n=12) after adoptive transfer of immunity on day 2 after infection.

It was surprisingly found that the topical combination of foscarnet and budesonide was superior in efficacy when compared to foscarnet cream and budesonide cream when tested separately (FIGS. 1, 2). The results show that the combination of foscarnet and budesonide is superior to placebo, foscarnet cream alone and budesonide cream alone in terms of inflammation (as measured by ear thickness) and lesion score. This is especially surprising because budesonide cream alone stimulates virus growth compared to placebo.

Experiment 2. Sequential Test of Foscarnet Cream and an Antiinflammatory Cream

This experiment was performed to extend the results obtained in Experiment 1 using the same animal model with ten animals in each group. Mixing of foscarnet and an antiinflammatory substance into one composition might not result in a formulation having optimal penetration properties for the two active compounds. In this experiment the animals were treated with two different formulations 2 hours apart. First the foscarnet cream was applied and 2 hours later the antiinflammatory formulation. This was repeated three times daily during the treatment period (day 4–7 after infection).

The tested substances as well as the results obtained, that is cumulative lesion score and cumulative ear thickness measured as in Experiment 1, are shown in Table 2 with the percent compared to placebo in parenthesis (values for placebo treated animals were set to 100%). Values significantly different form placebo-treated animals are indicated with an asterisk (p=0.0001).

TABLE 2

| Active substance (% w/w) | Mean cumulative value ± s.d. (% of placebo) Lesion score | Mean cumulative value ± s.d. (% of placebo) Ear thickness |
| --- | --- | --- |
| Placebo | 5.7 ± 1.3 (100) | 3.2 ± 0.3 (100) |
| Foscarnet | 4.8 ± 2.0 (84) | 2.8 ± 0.3 (88) |
| Foscarnet + Budesonide | 2.6 ± 1.0 (46)* | 1.9 ± 0.2 (59)* |
| Foscarnet + Hydrocortisone | 2.5 ± 1.1 (44)* | 1.7 ± 0.2 (53)* |
| Foscarnet + Lidocaine | 10.8 ± 1.5 (189) | 4.7 ± 0.4 (146)* |
| Foscarnet + Ketoprofen | 5.5 ± 1.4 (96) | 2.9 ± 0.3 (91) |

The following substances were tested: foscarnet (3%, Foscarnet Cream), budesonide (0.025%, Preferid®, Gist-Brocades, The Netherlands), hydrocortisone (1%, Hydrokortison kräm 1% ACO, Kabi Pharmacia AB, Sweden), lidocaine (5%, Xylocaine®, Astra AB) and ketoprofen (2.5%, Oruvail®, Rhone-Poulenc Rorer A/S, Denmark)

Foscarnet cream alone resulted in a small reduction in both lesion score and ear thickness in comparison to placebo which was not statistically significant. Foscarnet cream in combination with budesonide cream or with hydrocortisone cream was clearly superior to both foscarnet cream alone and placebo cream. Foscarnet cream in combination with budesonide cream reduced lesion score to 46% and ear thickness to 59% compared to placebo treated animals. Foscarnet cream in combination with hydrocortisone cream reduced lesion score to 44% and ear thickness to 53% compared to placebo treated animals. Foscarnet cream in combination with lidocaine cream worsened the lesion score and ear thickness to 189 and 146% of placebo-treated animals, respectively. Foscarnet cream in combination with ketoprofen cream had no effect on either lesion score or ear thickness. Two other NSAIDs, that is indomethacin (1%, Amuno® Gel, MSD Sharp & Dohme GmbH, Germany) and diclofenac (1.16%, Voltaren® Emulgel, Ciba-Geigy, GmbH, Germany) were also tested but the results could not be interpreted due to toxic side-effects. These side-effects were probably caused by systemic absorption of the NSAIDs in too high amounts.

As previously discussed, budesonide cream strongly increased the virus load in the animal model above compared with placebo (FIG. 1). This effect of budesonide is not beneficial for the treatment of herpes lesions. The virus titres in the ears of treated animals on day 7 after infection are shown in Table 3.

TABLE 3

| Treatment | Virus titre in the ear ($\log_{10}$pfu/ml) ± s.d. on d 7 |
| --- | --- |
| ATI −, placebo | 5.46 ± 0.35 |
| ATI +, placebo | 4.41 ± 0.09 |
| ATI +, foscarnet | 3.25 ± 0.49 |
| ATI +, foscarnet, hydrocortisone | 2.99 ± 0.28 |
| ATI +, foscarnet, ketoprofen | 2.62 ± 0.51 |
| ATI +, foscarnet, budesonide | 3.52 ± 0.16 |
| ATI +, foscarnet, lidocaine | 2.18 ± 0.51 |

Foscarnet cream alone reduced the virus titre on day 7 about tenfold compared to placebo-treated animals. Foscarnet cream in combination with hydrocortisone, ketoprofen, or lidocaine cream resulted in virus titres even lower than those in foscarnet-treated animals. Foscarnet cream in combination with budesonide resulted in virus titres on day 7 slightly higher than those of animals treated with foscarnet alone, but still nearly ten-fold lower than placebo-treated animals.

The results show that a combination of foscarnet with a glucocorticoid is clearly superior to combinations of foscarnet with a local anaesthetic or with ketoprofen as a non-steroid anti-inflammatory drug (NSAID) with regard to inflammation (as measured by ear thickness) and lesion score. The results also show that a foscarnet combination including hydrocortisone—a less potent glucocorticoid—was superior to foscarnet combinations including budesonide—a more potent glucocorticoid—in terms of all the measured parameters, that is cumulative lesion score, cumulative ear thickness and mean virus titres.

Experiment 3. Test of Combination Creams of an Antiviral and an Anti-inflammatory Substance This experiment was performed to extend the results of Experiment 2 by using acyclovir in addition to foscarnet, and also a combination with hydrocortisone. The same animal model with ten animals in each group was used. Animals were treated three times daily on days 4–7 after infection with different combination creams, with the formulation as follows:

foscarnet (3%, Foscarnet Cream), acyclovir (5%, Zovirax® Creme, Wellcome GmbH, Germany), hydrocortisone (1%, Hydrokortison kräm 1% ACO, Kabi Pharmacia AB, Sweden, Example 4), foscarnet+hydrocortisone (1.5%+ 0.5%, a 1:1 mixture of Foscarnet cream 3% and Hydrokortison kräm 1% ACO, Kabi Pharmacia AB), and acyclovir+hydrocortisone (2.5%+0.5%, a 1:1 mixture of Zovirax® Creme 5%, Wellcome GmbH and Hydrokortison 1% ACO, Kabi Pharmacia AB).

In addition, systemic treatment with acyclovir at 50 mg/kg injected intra-peritoneally three times daily was also used.

The substances tested and the results obtained (mean cumulative lesion score and mean cumulative ear thickness) are shown in Table 4, with the percent compared to placebo in parenthesis (values for placebo treated animals were set to 100%).

TABLE 4

| Active substance | Mean cumulative value ± s.d. (% of placebo) | |
| --- | --- | --- |
| (% w/w) | lesion score | ear thickness (mm) |
| Placebo | 6.8 ± 1.1 (100) | 3.3 ± 0.4 (100) |
| Foscarnet | 7.3 ± 1.2 (107) | 3.3 ± 0.2 (98) |

TABLE 4-continued

| Active substance (% w/w) | Mean cumulative value ± s.d. (% of placebo) | |
|---|---|---|
| | lesion score | ear thickness (mm) |
| Acyclovir | 8.0 ± 1.3 (118) | 3.3 ± 0.3 (100) |
| Hydrocortisone | 6.0 ± 1.3 (88) | 2.0 ± 0.2 (61)* |
| Acyclovir i.p. | 7.0 ± 1.6 (103) | 3.0 ± 0.4 (88) |
| Foscarnet + hydrocortisone | 6.2 ± 1.2 (91) | 2.0 ± 0.1 (61)* |
| Acyclovir + hydrocortisone | 6.9 ± 1.5 (101) | 2.2 ± 0.1 (66)* |

Figure 3:
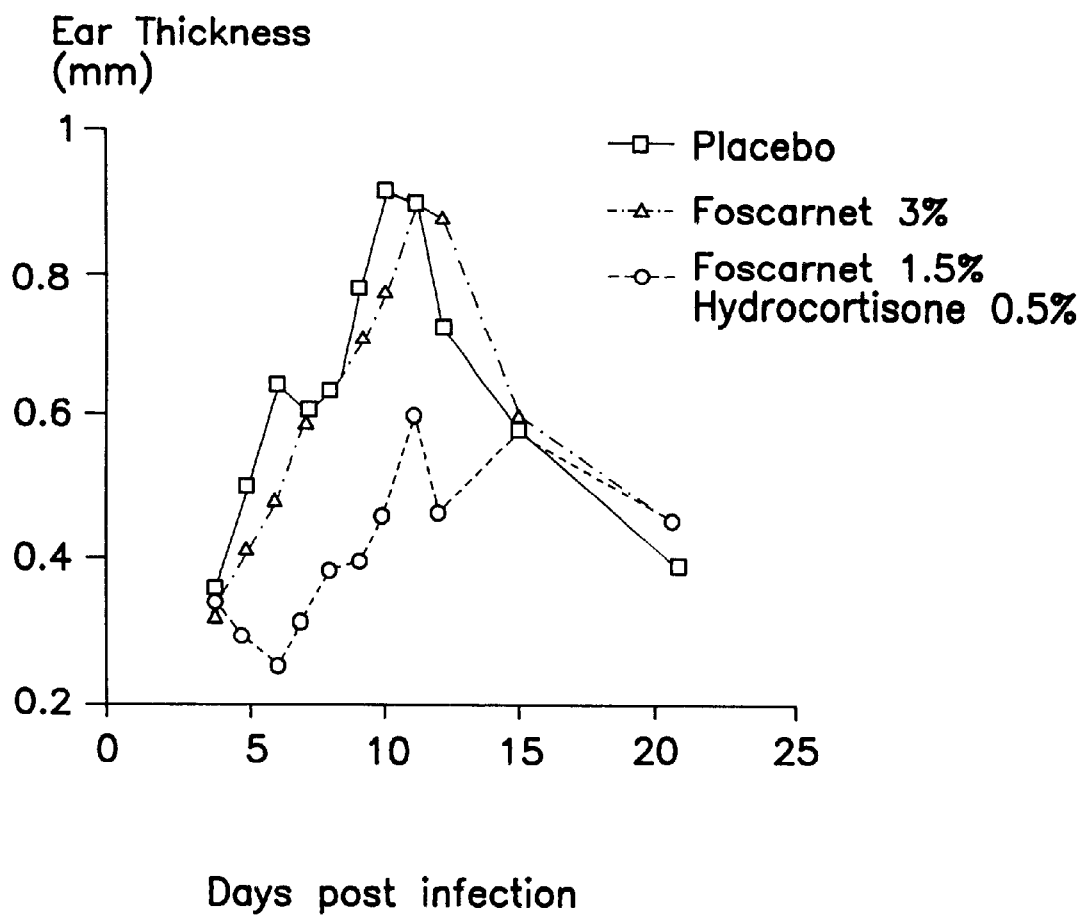
FIG. 3 Effects of topical treatment with foscarnet and foscarnet+hydrocortisone on days 4–7 after infection in comparison with placebo on mean ear thickness of neck-infected Balb/C mice (n=10) after adoptive transfer of immunity on day 2 after infection.

FIG. 3 shows the mean ear thickness on days 4–21 p.i. after treatment with placebo, 3% foscarnet or 1.5% foscarnet plus 0.5% hydrocortisone on days 4–7 p.i. The figure shows that foscarnet in combination with hydrocortisone was clearly superior in reducing the ear thickness compared to foscarnet alone or placebo.

The results of the above experiments show that topical administration of a combination of an antiviral substance and an antiinflammatory glucocorticoid in addition to reducing the virus titer also reduces the inflammatory symptoms characteristic of a recurrent herpes infection as measured by ear thickness and lesion score.

What is claimed is:

1. A pharmaceutical composition for topical administration comprising a synergistic combination of a topically acceptable antiviral substance which is 1) a herpes-specific nucleoside analogue or an ester, salt or solvate thereof that is preferentially phosphorylated in virus-infected cells or 2) selected from the group consisting of cidofovir, PMEA, PAA and PFA or an ester, salt or solvate thereof, and an antiinflammatory glucocorticoid in a pharmaceutically acceptable carrier.

2. A pharmaceutical composition for topical administration comprising a synergistic combination of a topically acceptable antiviral substance selected from the group consisting of acyclovir, cidofovir, desciclovir, famciclovir, ganciclovir, lobucavir, penciclovir, PMEA, valacyclovir, 2242, PAA, PFA and H2G or an ester, salt or solvate thereof and an antiinflammatory glucocorticoid in a pharmaceutically acceptable carrier.

3. A pharmaceutical composition according to claim 1, wherein the antiinflammatory glucocorticoid is selected from the group consisting of hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide or an ester, salt or solvate thereof.

4. A pharmaceutical composition according to claim 2, wherein the antiinflammatory glucocorticoid is selected from the group consisting of hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide or an ester, salt or solvate thereof.

5. A pharmaceutical composition according to claim 1, wherein the antiviral substance is foscarnet and the antiinflammatory glucocorticoid is hydrocortisone, or an ester thereof.

6. A pharmaceutical composition according to claim 1, wherein the antiviral substance is foscarnet and the antiinflammatory glucocorticoid is budesonide, or an ester thereof.

7. A pharmaceutical composition according to claim 1, wherein the antiviral substance is acyclovir, or an ester, salt or solvate thereof, and the antiinflammatory glucocorticoid is hydrocortisone, or an ester thereof.

8. The pharmaceutical composition according to claim 5 comprising 0.1–10% foscarnet and 0.005–3% hydrocortisone.

9. The pharmaceutical composition according to claim 8 comprising 1–5% foscarnet.

10. The pharmaceutical composition according to claim 8 comprising 0.3–3% foscarnet and 0.25–1% hydrocortisone.

11. The pharmaceutical composition according to claim 6 comprising 0.1–10% foscarnet and 0.005–3% budesonide.

12. The pharmaceutical composition according to claim 11 comprising 1–5% foscarnet.

13. The pharmaceutical composition according to claim 7 comprising 0.1–10% acyclovir and 0.005–3% hydrocortisone.

14. The pharmaceutical composition according to claim 13 comprising 1–5% acyclovir.

15. The pharmaceutical composition according to claim 14 comprising 0.25–1% hydrocortisone.

16. A cream, lotion, gel, ointment, plaster, stick or pen containing a pharmaceutical composition according to any one of claims 1–15.

17. A method for the prophylaxis and/or treatment of herpesvirus infections of the skin or mucous membranes in mammals comprising topical administration, in combination or in sequence, of a therapeutically synergistic dose of a topically acceptable antiviral substance which is 1) a herpes-specific nucleoside analogue or an ester, salt or solvate thereof that is preferentially phosphorylated in virus-infected cells or 2) selected from the group consisting of cidofovir, PMEA, PAA and PFA or an ester, salt or solvate thereof and an antiinflammatory glucocorticoid.

18. A method for the prophylaxis and/or treatment of herepesvirus infections of the skin or mucous membranes in mammals comprising topical administration, in combination or in sequence, of a therapeutically synergistic dose of a topically acceptable antiviral substance selected from the group consisting of acyclovir, cidofovir, desciclovir, famciclovir, ganciclovir, lobucavir, penciclovir, PMEA, valacyclovir, 2242, PAA, PFA and H2G or an ester, salt or solvate thereof and an antiinflammatory glucocorticoid in a pharmaceutically acceptable carrier.

19. A method according to claim 17, wherein the antiinflammatory glucocorticoid is selected from the group consisting of hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide or an ester, salt or solvate thereof.

20. A method according to claim 18, wherein the antiinflammatory glucocorticoid is selected from the group consisting of hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide or an ester, salt or solvate thereof.

21. A method according to claim 17, wherein the antiviral substance is foscarnet and the antiinflammatory glucocorticoid is hydrocortisone, or an ester thereof.

22. A method according to claim 17, wherein the antiviral substance is foscarnet and the antiinflammatory glucocorticoid is budesonide, or an ester thereof.

23. A method according to claim 17, wherein the antiviral substance is acyclovir, or an ester, salt or solvate thereof, and the antiinflammatory glucocorticoid is hydrocortisone, or an ester thereof.

24. A method for the prophylaxis and/or treatment of herpesvirus infections of the skin or mucous membranes in mammals comprising topical administration of a composition according to any one of claims 1–15.

25. A method according to claim 24 wherein the composition is contained in a cream, lotion, gel, ointment, plaster, stick or pen.

26. A method according to any one of claims 17–23, wherein the herpesvirus infection is a recurrent herpesvirus infection.

27. A method according to any one of claims 17–23, wherein the antiviral substance and the glucocorticoid are administered 1 to 10 times per day.

28. A method according to claim 27, wherein the antiviral substance and the glucocorticoid are administered 3 to 4 times per day.

29. A method according to claim 26, wherein the antiviral substance and the glucocorticoid are administered 1 to 10 times per day.

30. A method according to claim 29, wherein the antiviral substance and the glucocorticoid are administered 3 to 4 times per day.

31. A method according to any one of claims 17–23 wherein the antiviral substance and the glucocorticoid are administered in combination and are contained in a cream, lotion, gel, ointment, plaster, stick or pen.

32. A method according to claim 24, wherein the herpesvirus infection is a recurrent herpesvirus infection.

33. A method according to claim 24, wherein the antiviral substance and the glucocorticoid are administered 1 to 10 times per day.

34. A method according to claim 33, wherein the antiviral substance and the glucocorticoid are administered 3 to 4 times per day.

35. A method according to claim 31, wherein the antiviral substance and the glucocorticoid are administered 1 to 10 times per day.

36. A method according to claim 35, wherein the antiviral substance and the glucocorticoid are administered 3 to 4 times per day.

* * * * *

UNITED STATES PATENT AND TRADEMARK OFFICE
CERTIFICATE OF CORRECTION

PATENT NO. : 6,337,324  
DATED : January 8, 2002  
INVENTOR(S) : Harmenberg et al.

Page 1 of 1

It is certified that error appears in the above-identified patent and that said Letters Patent is hereby corrected as shown below:

<u>Column 16,</u>
Line 16, delete "claim 31" and substitute therefor -- claim 32 --.

Signed and Sealed this

Fourteenth Day of May, 2002

*Attest:*

*Attesting Officer*

JAMES E. ROGAN
*Director of the United States Patent and Trademark Office*